United States Patent

Linn et al.

[11] Patent Number: 5,972,319
[45] Date of Patent: Oct. 26, 1999

[54] ANTIPERSPIRANT STICK WITH IMPROVED CHARACTERISTICS

[75] Inventors: Elizabeth Linn, Lyndhurst; Kathy J. Potechin, Short Hills, both of N.J.

[73] Assignee: The Colgate-Palmolive Company, NY, N.Y.

[21] Appl. No.: 08/829,399

[22] Filed: Mar. 31, 1997

[51] Int. Cl.⁶ .................................................. A61K 7/32
[52] U.S. Cl. .............................. 424/65; 424/66; 424/68; 424/401; 424/498
[58] Field of Search ................. 424/401, 65, 66, 424/68, 498, 717, DIG. 5, 78.03

[56] References Cited

U.S. PATENT DOCUMENTS

| | | | |
|---|---|---|---|
| 4,202,879 | 5/1980 | Shelton | 424/66 |
| 4,275,222 | 6/1981 | Scala, Jr. | 560/103 |
| 4,278,655 | 7/1981 | Elmi | 424/47 |
| 4,278,658 | 7/1981 | Hooper et al. | 424/65 |
| 4,293,544 | 10/1981 | Elmi | 424/60 |
| 4,322,545 | 3/1982 | Scala, Jr. | 560/103 |
| 4,323,693 | 4/1982 | Scala, Jr. | 560/103 |
| 4,323,694 | 4/1982 | Scala, Jr. | 560/103 |
| 4,550,035 | 10/1985 | Smith | 427/398.1 |
| 4,719,104 | 1/1988 | Patel | 424/70 |
| 4,725,432 | 2/1988 | May | 424/66 |
| 4,791,097 | 12/1988 | Walele et al. | 560/112 |
| 4,822,603 | 4/1989 | Farris et al. | 424/66 |
| 4,917,882 | 4/1990 | Strobridge | 424/401 |
| 4,919,934 | 4/1990 | Deckner et al. | 424/401 |
| 4,985,238 | 1/1991 | Tanner et al. | 424/66 |
| 5,082,652 | 1/1992 | Mayfield et al. | 424/47 |
| 5,169,626 | 12/1992 | Tanner et al. | 424/66 |
| 5,225,188 | 7/1993 | Abrutyn et al. | 424/66 |
| 5,254,332 | 10/1993 | Greczyn et al. | 424/66 |
| 5,302,381 | 4/1994 | Greczyn et al. | 424/66 |
| 5,449,511 | 9/1995 | Coe | 424/66 |
| 5,456,906 | 10/1995 | Powell et al. | 424/66 |
| 5,531,986 | 7/1996 | Shevade et al. | 424/68 |

FOREIGN PATENT DOCUMENTS

| | | |
|---|---|---|
| 0 295 071 A2 | 12/1988 | European Pat. Off. . |
| 0 357 628 B1 | 1/1994 | European Pat. Off. . |
| 0 659 403 A2 | 6/1995 | European Pat. Off. . |
| 2 299 024 | 3/1995 | United Kingdom . |
| 2 291 805 | 2/1996 | United Kingdom . |
| 93/10131 | 5/1993 | WIPO . |
| 94/13255 | 6/1994 | WIPO . |
| WO 94/13256 | 6/1994 | WIPO . |
| WO 94/24997 | 11/1994 | WIPO . |
| WO 94/28866 | 12/1994 | WIPO . |
| WO 97/34577 | 3/1997 | WIPO . |
| WO 97/48373 | 6/1997 | WIPO . |

OTHER PUBLICATIONS

*Finetex® Inc.,* "Antiperspirants and Deodorants Containing Finsolv® TN," p. 1–2.
*Finetex® Inc.,* "Finsolv® TN," Nov., 1995, pp. 1–4. (undated).

*Primary Examiner*—Jose' G. Dees
*Assistant Examiner*—Kathryne E. Shelborne
*Attorney, Agent, or Firm*—Rosemary M. Miano

[57] ABSTRACT

Disclosed are antiperspirant stick compositions that exhibit substantially less visible residue (whitening) upon application to the skin or after drying and which exhibit improved aesthetics and superior cosmetic properties. The compositions include (a) non-volatile emollients that are not silicone materials and which have (individually or as a mixture) a refractive index of at least 1.4460, and which have adsorption and desorption properties relative to the antiperspirant material sufficient to achieve the desired reduction in residue (whiteness); (b) a vehicle (for example, cyclomethicone), (c) a gelling agent (for example, stearyl alcohol and hydrogenated castor oil); (d) at least one active antiperspirant material (for example, particulate antiperspirant metal salts); and (e) a surfactant.

35 Claims, No Drawings ns ANTIPERSPIRANT STICK WITH
IMPROVED CHARACTERISTICS

BACKGROUND OF THE INVENTION

The present invention is directed to an antiperspirant stick composition which has improved aesthetics, which leaves less visible (for example, white) residue on skin after application or after drying, and which has superior cosmetic properties.

Wax-based stick compositions, which contain a wax-type solidifying agent, are known. It is also known to incorporate an antiperspirant active material, such as aluminum-zirconium-glycine complexes, in such wax-based stick compositions, to provide an antiperspirant stick. However, application of such wax-based antiperspirant stick product to the skin frequently results in objectionable aesthetic characteristics (such as unsatisfactory glide on the skin); moreover, such products unsatisfactorily leave visible residue (white residue) on the skin after application and after drying.

U.S. Pat. No. 4,919,934 to Deckner, et al. discloses wax-based cosmetic stick compositions containing specific amounts of a wax-type solidifying agent and a polyalphaolefin, and preferably an active component such as a sunscreen agent, analgesic, antiperspirant or deodorant active. This patent discloses that the stick composition preferably also includes at least one emollient, selected from as volatile and non-volatile silicone oils and non-polar fatty acid and fatty alcohol esters, and that compositions which contain an antiperspirant active and/or deodorant active also preferably include at least one emulsifier. The contents of U.S. Pat. No. 4,919,934 are incorporated herein by reference in their entirety.

Various emollients have been suggested for use in cosmetic sticks such as antiperspirant/deodorant product. Some of these are described in U.S. Pat. No. 4,202,879 to Shelton and U.S. Pat. No. 4,725,432 to May. Examples of such emollients include fatty acid and fatty alcohol esters and water insoluble ethers There have been attempts to provide low-residue antiperspirant solid sticks. See, for example, U.S. Pat. No. 4,822,603 to Farris, et al.; U.S. Pat. No. 5,254,332 to Greczyn, et al.; and U.S. Pat. No. 5,302,381 to Greczyn, et al. Each of U.S. Pat. No. 4,985,238 to Tanner and U.S. Pat. No. 5,169,626 to Tanner discloses low residue antiperspirant sticks containing specific amounts of a volatile silicone material; a particulate antiperspirant active; a low melting point wax; and a non-volatile paraffinic hydrocarbon fluid selected from mineral oils, branched-chain hydrocarbons containing an average of from about 16 to about 68 carbon atoms, and mixtures thereof. Non-essential components which can also be incorporated in the sticks include, for example, emollients, colorants, perfumes and emulsifiers.

U.S. Pat. No. 5,225,188 to Abrutyn, et al. discloses underarm formulations which contain volatile and/or non-volatile alkylmethylsiloxanes having a specific structure, which formulations may contain other components such as astringent antiperspirant compounds, suspending agents, conventional waxes, emollients, perfumes, coloring agents and other ingredients normally used in making underarm products. Incorporation of the alkylmethylsiloxanes in underarm formulations provide characteristics such as modified hardness, reduced whitening, improved feel, compatibility of ingredients, and control of vapor pressure.

It has also been proposed to incorporate phenyltrimethicone in antiperspirant formulations containing cyclomethicone as a vehicle, stearyl alcohol and hydrogenated castor oil as gelling agents, PEG-8 distearate, and aluminum-zirconium-tetrachlorohydrex-Gly, the phenyltrimethicone acting as a masking ingredient for the antiperspirant active ingredient to avoid a visible residue of the antiperspirant active on the skin.

U.S. Pat. No. 5,449,511 to Coe, the contents of which are incorporated herein by reference in their entirety, discloses a non-aqueous antiperspirant product that includes a non-aqueous carrier vehicle; an antiperspirant active salt suspended in particle form in the carrier vehicle; and a non-volatile, water-soluble, liquid (at 25 degrees C.) masking agent that interacts with the antiperspirant active to essentially eliminate discernible whitening without substantially inhibiting the antiperspirant activity of the salt when the product is applied to the skin. The masking agent can be a non-volatile aliphatic compound (such as alcohols, ethers, silanols, silyl ethers, siloxanes and silicones) which contains disubstituted oxygen functionalities. This patent discloses that the masking agent preferably is a water-soluble, liquid, non-volatile emollient material, which reduces whitening by interacting with the particulates to produce an optical effect that tends to reduce light scattering and apparent whiteness. Illustrative masking agents disclosed in U.S. Pat. No. 5,449,511 include PPG-10 butanediol and dimethicone copolyols. This patent discloses that, in addition, for solid products, gelling agents may be included, examples of suitable gelling agents including hydrogenated castor oil, and fatty alcohols such as stearyl alcohol, among others, as well as blends and combinations.

U.S. Pat. 5,531,986 to Shevade et al describes a low residue antiperspirant solid stick containing volatile and non-volatile silicone materials, dimethicone copolyol and high-melting and low-melting point waxes.

There have also been efforts to develop cosmetic compositions with improved aesthetics. U.S. Pat. No. 5,082,652 to Mayfield et al teaches the use of an oil absorbent particulate material to prevent dusting of liquid particles and the addition of a silicone polymer to prevent dusting by the oil absorbent particulate material.

U.S. Pat. No. 4,917,882 to Strobridge discloses a gel-type sunscreen comprising polyethylene and an ester of benzoic acid and C12–C15 alcohols. The product is described as having a generally non-greasy feel and uses the benzoate ester to provide a translucent, anhydrous vehicle for the sunscreen.

U.S. Pat. No. 4,278,655 to Elmi teaches the use of benzoic acid esters made with C9–C15 linear primary alcohols as liquid carriers in a pump spray, pressurized aerosol or roll-on antiperspirants. The compositions (which also contain a suspending agent) exhibit a reduction in oily sensation.

U.S. Pat. No. 4,323,693 to Scala discloses a substantially pure benzoic acid ester of isostearyl (C18) alcohol. This reference discloses that this ester has a lack of greasiness.

Notwithstanding the foregoing, it is still desired to provide an antiperspirant stick composition that exhibits substantially less whitening (residue) upon application to the skin or after drying thereon, which has desired cosmetic properties and antiperspirant efficacy, which has improved feel to the skin (in particular, reduced oiliness), better glide upon application and less tack.

It is a first object of the present invention to provide an antiperspirant stick composition which leaves less residue after application and drying than conventional antiperspirant stick products.

It is a further object to provide an antiperspirant stick composition having substantially reduced visible (white)

residue on the skin after application and, after drying, an improved and less oily feel to the skin, and a method of making and using such antiperspirant stick composition.

It is yet another object of the present invention to provide an antiperspirant stick composition which exhibits substantially less visible residue on the skin after application and after drying, and which has good cosmetic properties (including good glide on the skin and good emolliency) and antiperspirant efficacy.

SUMMARY OF THE INVENTION

The foregoing objects are achieved by an antiperspirant stick composition which comprises:

(1) a gelling agent, in an amount so as to form a stick (for example, a solid stick) product wherein the gelling agent (which can be one agent or two or more agents in combination) is selected from the group consisting of high melting point waxes (150–215 degrees F. (65–101 degrees C.)) and low melting point waxes (100–150 degrees F. (37–65 degrees C.)), including silicone waxes such as stearoxytrimethylsilane;

(2) a vehicle (also called a solvent) for the gelling agent, in a type and amount such that the gelling agent can dissolve therein and can gel therefrom, wherein the solvent is selected from the group consisting of volatile cyclic silicones and aliphatic hydrocarbons;

(3) an effective amount of a cosmetically active material, for example, an active material selected from conventional antiperspirant active metal salts;

(4) a non-volatile emollient that is not a silicone fluid material, which has a refractive index of at least 1.4460, and which has adsorption and desorption properties relative to the active material (such as an antiperspirant material), wherein this emollient material:

(i) is present in an amount so as to reduce a whitening effect of the active material, such as the antiperspirant active ingredient, on the skin; and (ii) is selected from the group consisting of (a) esters which are not otherwise classified as alkoxylated carboxylic acids, glyceryl esters, isethionates, lanolin derivatives, phosphorous compounds, sulfosuccinates or sulfuric acid esters;

(b) alkoxylated alcohols wherein the alcohol portion is selected from aliphatic alcohols having 2–18 carbons (for example, 2–10 carbons and, more particularly, from 2–6 carbons); and the alkylene oxide portion is selected from the group consisting of ethylene oxide, polyoxyethylene, and polyoxypropylene having a number of alkylene units from 2–53 (for example, 4–30 units and, more particularly, from 12 to 15 units).

(5) a surfactant selected from the group consisting of ethoxylated fatty acids having 2–20 ethoxylate groups and made from fatty acids having 12–18 carbons.

Illustratively, compositions according to the present invention include the following components in the amounts indicated (where the percents are percent by weight based on the total weight of the composition): 17–40% gelling agent; 30–50% solvent; 10–30% antiperspirant active; 10–27% nonvolatile emollient; and 1–15% surfactant.

DETAILED DESCRIPTION OF THE INVENTION

In formulating compositions of the present invention gelling agents may be selected from those known in the art, provided that the gelling agent (which may also be a combination of two or more agents) is soluble in the vehicle and able to be gelled therefrom. For example, the composition is heated in order to dissolve the gelling agent in the vehicle and gelling occurs upon cooling of the composition. In particular, the gelling agent may be selected from the group consisting of high melting point waxes (including beeswax, montan, ozokerite, ceresin, paraffin, synthetic waxes, hydrogenated castor oil); low melting point waxes (including fatty alcohols containing from about 8–20 carbons);and silicone waxes. A more particular group of gelling agents consists of stearyl alcohol and hydrogenated castor oil. The gelling agent is then combined with a vehicle (also called a solvent) to form the gelling composition.

For an overall discussion of gelling agents, attention is directed to the solidifying agents described in U.S. Pat. No. 4,919,934 to Deckner et al, the contents of which have been incorporated herein by reference in their entirety. Examples of such gelling agents include crystalline waxes, cetyl stearate, stearyl stearate, cetyl myristate, cetyl palmitate, stearoxydimethicone, and microcrystalline waxes.

Various combinations, blends and mixtures of different materials can be utilized as the gelling agent according to the present invention. Examples of such blends or mixtures include stearyl alcohol and beeswax or cetyl alcohol and hydrogenated castor oil.

Illustratively, the gelling agent is included in an amount of 17–40 percent by weight of the total weight of the composition, particularly in an amount of 20–26 percent.

Where the gelling agent includes both high and low melting point waxes, the low melting point wax is included in the composition in an amount of 10–25 percent by weight, particularly 15–23 percent, and the high melting point wax is included in the composition in an amount of 2–17 percent by weight of the total weight of the composition, particularly 2–8 percent. Examples of such combinations of waxes include 15–23 percent stearyl alcohol and 2–8 percent beeswax, or 15–23 percent cetyl alcohol and 2–8 percent hydrogenated castor oil.

A solvent or vehicle can be selected from the group consisting of volatile cyclic polydimethylsiloxanes; and aliphatic hydrocarbons having 10 to 32 carbons, for example 10 to 20 carbons. A particular solvent is cyclomethicone represented by the formula

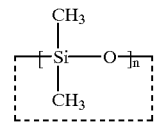

where n is an integer with a value of about 3–7, and particularly a value of 5–6.

By volatile silicone material, we mean a material that has a measurable vapor pressure at ambient temperature. Illustratively DC-345 silicone fluid from Dow Corning Corp., Midland, Mich. is a type of cyclomethicone which can be used. It should be noted that the vehicle is not limited to cyclomethicone and other suitable vehicles can be used. Examples of such other vehicles include aliphatic hydrocarbons such as hydrogenated polyisobutene, isodecane, isohexadecane and isoeicosane.

The solvent (vehicle) is included in the composition in an amount of 30–50 percent by weight of the total weight of the composition, particularly 35–45 percent and, more particularly, 36–42 percent.

Of course the gelling agent must be soluble in the vehicle, and must be able to be gelled therefrom, for example, upon cooling of the composition after the composition has been heated in order to dissolve the gelling agent in the vehicle.

The cosmetically active material can be selected from the group consisting of antiperspirants, deodorants, sunscreens and the like with antiperspirant actives being of particular interest. The antiperspirant active material can be any conventional antiperspirant material, including (but not limited to) antiperspirant active metal salts such as aluminum-zirconium tri-, tetra- and penta-chlorohydrate glycine complexes, which are coordination complexes of aluminum-zirconium tri-, tetra- or pentachlorohydrate and glycine in which some of the water molecules normally coordinated to the metal have been displaced by the glycine. Illustrative antiperspirant active metal salts include aluminum-zirconium tetrachlorohydrex gly (for example, Reach AZP-908 and Reach 908-0, each manufactured by Reheis Inc., (Berkeley Heights, N.J.), which are coordination complexes of aluminum-zirconium tetrachlorohydrate and glycine in which some of the water molecules normally coordinated to the metal have been displaced by the glycine. The present invention is not limited to use of aluminum-zirconium tetrachlorohydrex gly, and other antiperspirant active metal salts (such as aluminum chlorohydrate), and/or other antiperspirant active materials, can be utilized in the stick composition of the present invention.

Illustratively, antiperspirant solid stick compositions according to the present invention contain the antiperspirant active material in an amount of 10–30 percent by weight of the total weight of the composition, particularly 15–25 percent and, more particularly 18–23 percent. Moreover, the preferred antiperspirant material particulate (for example, antiperspirant salt particulate) has a median particle size of less than 100 microns. Most preferred is a median particulate size of 5–40 microns, preferably 5–10 microns.

Emollients are a known class of materials in this art, imparting a soothing effect to the skin. According to the present invention, the emollient (for example, non-volatile emollient) selected for and incorporated in the composition of the invention both reduces visible residue and imparts emollient effects to the skin.

For the compositions of this invention it has been found that emollients which are non-volatile emollients that are not silicone materials, which have a refractive index (individually or in a mixture) of at least 1.4460, and which have adsorption and desorption properties relative to the antiperspirant material, wherein this emollient material
  (i) is present in an amount so as to reduce a whitening effect of the antiperspirant active ingredient on the skin; and
  (ii) is selected from the group consisting of
    (a) esters which are not otherwise classified as alkoxylated carboxylic acids, glyceryl esters, isethionates, lanolin derivatives, phosphorous compounds, sulfosuccinates or sulfuric acid esters;
    (b) alkoxylated alcohols wherein the alcohol portion is selected from aliphatic alcohols having 2–18 and more particularly from 4 to 18, and the alkylene oxide portion is selected from the group consisting of ethylene oxide, polyoxyethylene, and polyoxypropylene having a number of alkylene units from 2–53 and more particularly from 2 to 15 units) are especially useful.

Examples of suitable emollients include isostearyl isostearate, isostearyl palmitate, benzyl laurate, PEG 12 and especially alkyl benzoates such as C12–C15 linear alkyl benzoates.

The non-volatile emollients can include mixtures. Examples of such mixtures include isostearyl isostearate and C12–C15 alkylbenzoate; and isostearyl benzoate and benzyl laurate.

Preferably, the emollient materials have a high refractive index which is also close to the refractive index of the antiperspirant active material. It is preferred that each of the emollient materials has a refractive index of at least 1.4460. Also it is preferred that the emollient material has adsorption and desorption onto the active material of at least 10 millijoules/gram ("mJ/g") for each property as measured by the tests described below. More preferably the adsorption value should be at least 15 mJ/g and the desorption value should be at least 10 mJ/g where the values are measured by FMC (flow microcalorimetry). By incorporating emollients having suitable adsorption and desorption properties and a refractive index of at least 1.4460 into the composition, both improved cosmetic properties and reduced whitening effects are achieved. The refractive indices of the emollient (or emollients), and the ability of the emollient to adsorb onto the antiperspirant active are selected so as to reduce and minimize the whitening effects of the antiperspirant salt and other whitening ingredients in the composition (such as talc). In addition, the emollient has the ability to desorb from the active to allow for maximum antiperspirant efficacy.

The composition according to the present invention desirably includes, in addition to the foregoing components, at least one member selected from the group consisting of surface active agents (surfactants), inert fillers and/or other materials such as, for example, fragrance, bacteriostats, bactericides, coloring agents, thickeners, and antioxidants.

Surfactants may be included in the compositions of the invention. Illustratively such surfactants include alkanolamides (such as N-alkyl pyrrolidone), ethoxylated amides (for example, the polyethylene glycol amide of tallow acid that conforms generally to the formula RC(O)—NH—(CH$_2$CH$_2$O)$_n$H where RCO— represents the fatty acids derived from tallow and n has an average value of 50 (also called PEG-50 tallow amide)); amine oxides (for example, cocamidopropylamine oxide); ethoxylated fatty acids (for example, the polyethylene glycol diester of stearic acid that conforms generally to the formula CH$_3$(CH$_2$)$_{16}$C(O)—(OCH$_2$CH$_2$)$_n$O—C(O)(CH$_2$)$_{16}$CH$_3$ (also called PEG-8 distearate)); ethoxylated glycerides (for example, a polyethylene glycol derivative of Castor Oil with an average of 4 moles of ethylene oxide (also called PEG-4 castor oil)); glycol esters (for example, propylene glycol ricinoleate); monoglycerides (for example, glycerol myristate); polyglyceryl esters (for example, polyglyceryl-4 oleyl ether); polyhydric alcohol esters and ethers (for example, sucrose distearate); sorbitan/sorbitan esters (for example, sorbitan sesquiisostearate); triesters of phosphoric acid (for example, trioleth-8 phosphate (a material which is predominantly the triester of phosphoric acid and ethoxylated oleyl alcohol with an average of 8 moles of ethylene oxide)); ethoxylated lanolin (for example, a polyethylene glycol derivative of Lanolin with an average of 20 moles of ethylene oxide (also called PEG-20 lanolin)); propoxylated polyoxyethylene ethers (for example, the polyoxypropylene, polyoxyethylene ether of cetyl alcohol that conforms generally to the formula

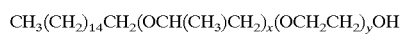

where x has an average value of 5 and y has an average value of 20 (also called PPG-5 ceteth-20)); and alkylpolyglycosides (for example, lauryl glucose). The surfactant (or surfactant blend) includes non-ionic compounds, and can also include blends thereof with cationic (for example, the polyethylene glycol amine of tallow acid that conforms generally to the formula R—NH—(CH$_2$CH$_2$O)$_n$H (n=15, also called PEG-15 tallow amine)) or anionic (for example, sodium lauroyl laurate which is the sodium salt of the lauric acid ester of lauric acid) surfactants.

The surfactant or blend thereof incorporated in compositions according to the present invention can, illustratively, be included in amounts of 1–15%, preferably 1–10 %, and most preferably 2–6% by weight, of the total weight of the composition.

Inert fillers can be incorporated in the antiperspirant stick compositions of the present invention. Illustratively, the inert filler can be corn starch, talc, fumed silica and/or inorganic clays, polyethylene, or mixtures of these inert particulate materials.

Where the inert filler contributes to the whitening (visible residue) effect of the stick composition, the whitening effect can be reduced through use of an emollient having the refractive index in the present invention.

Various fragrances known in the art can also be incorporated in the antiperspirant solid stick composition of the present invention. These fragrances can be incorporated in amounts known in the art, for example, 0.5–3.0% by weight, of the total weight of the composition.

Known bacteriostats include bacteriostatic quaternary ammonium compounds such as 2-amino-2-methyl-1-propanol (AMP), cetyl-trimethylammonium bromide, cetyl pyridinium chloride, 2, 4, 4N-trichloro-2N-hydroxydiphenylether (Triclosan), N-(4-chlorophenyl)-N'-(3,4-dichlorophenyl)urea (Triclocarban) and various zinc salts. The bacteriostat can, illustratively, be included in the composition in an amount of 0.05–1.0% by weight, of the total weight of the composition.

Accordingly, through use of the present invention, incorporating at least one, non-volatile emollient material having a refractive index of at least 1.4460 in the composition, an antiperspirant stick composition is achieved which exhibits reduced residue (whitening) upon application to the skin or after drying, and which composition has good cosmetic properties.

The present invention contemplates as a preferred embodiment an antiperspirant stick composition that leaves substantially less visible residue (whitening) either upon application to the skin or after drying on the skin. The composition includes, in addition to an antiperspirant active material (for example, a particulate antiperspirant metal salt), a gelling agent, a vehicle for the gelling agent (the vehicle being a material in which the gelling agent can dissolve and from which the gelling agent can form a gel (for example, upon cooling)), and an emollient, the emollient including at least one non-volatile emollient material having a refractive index of at least 1.4460, and having an adsorption value and desorption value of at least 10 mJ/g each when measured by flow microcalorimetry. The emollient is included in an amount so as to reduce the whitening effect of the antiperspirant active ingredient (and any other whitening powder ingredient, such as talc).

In the following Table are set forth various illustrative non-volatile emollient materials that can be utilized as part of the present invention, both to reduce the whitening effect of the antiperspirant active ingredient and to provide emollient properties to the antiperspirant stick compositions. Listed in the following Tables I and IA are the CTFA name (as set forth in the *CTFA International Cosmetic Ingredient Dictionary* (6th Ed. 1995)), a trade name for the material (where appropriate), and the refractive index of such material.

TABLE I[a]

| CTFA Name (for Esters) | Trade-name | Refractive Index |
|---|---|---|
| C12–C15 Alkyl benzoate | FINSOLV TN | 1.4820 |
| Octyldodecyl benzoate | FINSOLV BOD | 1.4833 |
| Isostearyl benzoate | FINSOLV SB | 1.4820 |
| Isostearyl lactate | PALEMOL ISL | 1.4519 |
| Isostearyl palmitate | DERMOL ISP | 1.4546 |
| Isostearyl isostearate | SCHERCEMOL 1818 | 1.4612 |
| Benzyl laurate | MAZON EE-1 | 1.4811 |
| Glycereth 7 benzoate | PALEMOL G7B | 1.4953 |

TABLE IA[b]

| CTFA Name (for Alkoxylated alcohols) | Trade-name | Refractive Index |
|---|---|---|
| Laureth 4 | MACOL LA 4 | 1.4514 |
| Laureth 7 | MACOL LA 790 | 1.4547 |
| Oleth-2 | BRIJ 93 | 1.4612 |
| PEG 4 | CARBOWAX 200 | 1.4594 |
| PEG 12 | CARBOWAX 600 | 1.4664 |
| PPG 2 ceteareth 9 | EUMULGIN L | 1.4611 |
| PPG 2 isodeceth 12 | SANDOXYLATE SX 424 | 1.4591 |
| PPG 5 buteth 7 | UCON 50 HB 170 | 1.4526 |
| PPG 14 butyl ether | FLUID AP | 1.4460 |
| PPG 15 butyl ether | UCON LB 285 | 1.4479 |
| PPG 53 butyl ether | UCON LB 3000 | 1.4512 |

[a,b]FINSOLV is a trademark of Finetex Inc.
BRIJ is a trademark of ICI Specialty Chemicals.
PELEMOL is a trademark of Phoenix Chemical, Inc.
EUMULGIN is a trademark of Henkel Corporation.
CARBOWAX is a trademark of Union Carbide Corporation.
UCON is a trademark of Union Carbide Corporation
MACOL is a trademark of PPG Industries, Inc.
SANDOXYLATE is a trademark of Sandoz Chemicals Corporation.

Of course, combinations (for example, mixtures) of at least two of the above-listed emollient materials can be incorporated in compositions of the present invention. Some non-limiting examples of combinations have been described above.

It is preferred that emollients having relatively high refractive indices close to that of, for example, the antiperspirant active ingredient, be utilized in order to avoid visible residue (whitening ) on the skin.

Table II describes selected emollients and the adsorption and desorption properties as measured by flow microcalorimetry. In this test a MICROSCAL Flow Microcalorimeter (from MICROSCAL LTD, London, United Kingdom) is used to quantify thermal effects due to interactions between the antiperspirant active salt surface and the emollient liquid. The instrument consists of a flow microcalorimeter housed in a draft proof enclosure with two syringe pumps located on the top of the enclosure. A downstream detector, the FMC control unit, a chart recorder and a computer are located next to the FMC unit. The microcalorimeter cell (0.17 ml in volume) is made of polytetrafluoroethylene (such as TEFLON) fitted in a metal block within the draft proof enclosure. Inlet and outlet connectors enclose the cell. The cell is filled with antiperspirant active salt which is carefully weighed. Cyclomethicone is the carrier solvent and is added from one of the two syringe pumps. It is passed through the cell via the connectors at a constant flow rate for example, at a rate of 0.66 ml/hour. The resulting effluent then flows through a downstream detector where its concentration is monitored. Temperature changes in the microcalorimeter cell due to the adsorption or desorption of the emollient solution onto the solid active salt are detected by two thermisters adjacent to the cell. The detected signals are transmitted to both a chart recorder and a computer to record the change in temperature as a function of time. An experiment to study adsorption/desorption of emollient onto an active salt (solute onto solid adsorbent) would involve three steps. The first step is to establish a baseline by wetting the active salt with cyclomethicone supplied by one of the syringe pumps. In the second step a portion of the emollient solution in cyclomethicone from the other syringe pump is introduced and flown passed the active salt bed long enough for the adsorption of the emollient onto the active salt to reach equilibrium. In the third step the flow is switched back to cyclomethicone whereby the desorption process is monitored. The areas under the peaks are analyzed by the CALDOS software (from MICROSCAL LTD.) and the results are shown in Table II.

The adsorption and desorption data measures the amount of heat given off due to adsorption on to the antiperspirant active and the amount of heat absorbed due to desorption from the active.

TABLE II

| CTFA Name | Trade-name | Adsorption energy (mJ/g) | Desorption energy (mJ/g) |
|---|---|---|---|
| C12–C15 Alkyl benzoate | FINSOLV TN | 27.4 | 13.2 |
| Isostearyl benzoate | FINSOLV SB | 39.1 | 37.6 |
| Octyldodecyl benzoate | FINSOLV BOD | 17.6 | 20.6 |
| Phenyltri-methicone | Dow Corning 556 | 0 | 0 |
| PPG 14 butyl ether | Fluid AP | 103.9 | 0 |
| Benzyl laurate | MAZON EE-1 | 64.2 | 29.1 |
| Isostearyl isostearate | SCHERCEMOL 1818 | 44.8 | 16.6 |

Illustratively, the non-volatile emollient can be incorporated in the composition in an amount of 10%–27% by weight, of the total weight of the composition, particularly 10–20%, and more particularly 10–15%.

It is preferred that emollients having relatively high refractive indices close to that of, for example, the antiperspirant active ingredient, be utilized, in order to avoid visible residue (whitening) on the skin.

The antiperspirant sticks of the present invention may be manufactured using methods known in the art. Typically, the ingredients are combined and heated to melt components (for example, other than the antiperspirant material particulate and particulate inert filler), and the melted and particulate components are mixed. Desirably, volatile materials, such as the fragrance material, are incorporated in the composition in the latter stages of the mixing cycle, in order to avoid volatilization thereof. After mixing, the molded composition can be poured into stick-form molds (for example, dispensing containers), as conventional in the art, after which the compositions harden into a solid.

The compositions according to the present invention can be utilized by the consumer, to reduce perspiration, as conventional antiperspirant solid stick compositions are used. The end of the molded compositions, hardened in the dispensing container, can be elevated out of the dispensing container, so as to protrude out of the dispensing container, and rubbed against the skin in the axillary region, for example, so as to deposit antiperspirant active material in the axillary region, which prevents (or at least reduces) perspiration from the axillary region. Thus, by rubbing the composition of the present invention against the skin in regions of the body particularly prone to perspiration (for example, the axillary region), perspiration wetness in such regions can be controlled.

EXAMPLES I and II

The following description sets forth examples of the present invention. This example is illustrative, and not limiting, of the present invention. In these examples, the amounts are in percent by weight, of the total weight of the composition. Where appropriate, the refractive indices of the various materials are set forth.

The emollient (C12–C15 alkyl benzoate) and gelling agents were combined, heated to a temperature in the range of 70–75 degrees C., and mixed until the waxes were melted and the mixture was uniform. The surfactant (PEG 8 distearate) was added and mixing was continued until the mixture was homogeneous. The volatile silicone vehicle (cyclomethicone) was slowly added while maintaining the temperature in the range of 70–75 degrees C. The aluminum salt was added in increments while maintaining the temperature at 70–75 degrees C. The mixture was cooled to 65 degrees C. and fragrance was added. The mixture was cooled further and poured into containers.

| Ingredients | Example I (% w/w) | Example II (% w/w) | Refractive Index |
|---|---|---|---|
| Cyclomethicone | 37.0 | 37.0 | 1.3980 |
| C12–C15 alkyl benzoate | 10.0 | 00.0 | 1.4820 |
| Aluminum Zirconium Tetrachlorohydrex Gly Complex | 24.0 | 22.0 | 1.5360 |
| PEG 8 Distearate | 4.0 | 4.0 | |
| Fragrance/Starch | 1.0 | 1.0 | |
| Hydrogenated Castor Oil | 4.0 | 4.0 | 1.570–1.585 |
| Stearyl alcohol | 20.0 | 20.0 | 1.50–1.52 |
| Isostearyl benzoate | 00.0 | 12.0 | 1.4820 |
| TOTAL | 100.0% | 100.0% | |

In the foregoing examples, C12–C15 alkyl benzoate and Isostearyl benzoate are used as the emollient materials reducing the whitening effect of the whitening powder ingredients (for example, the antiperspirant active material) on the skin.

EXAMPLE I AND COMPARATIVE EXAMPLE A

Example I as described above and Comparative Example A (a commercially available antiperspirant stick were compared on the basis of application parameters, for example, glide, comfort in application, stickiness, messiness, and oily feel. In all of these categories the composition made according to Example I was perceived as superior in application aesthetics than Comparative Example A.

| Ingredients | Example I (% w/w) | Comparative Example A (% w/w) |
|---|---|---|
| Cyclomethicone | 37.0 | 52.50 |
| C12–C15 alkyl benzoate | 10.0 | 00.0 |
| Aluminum Zirconium Tetrachlorohydrex Gly Complex | 24.0 | 22.0 |
| PEG 8 Distearate | 4.0 | 00.0 |
| Fragrance/Starch | 1.0 | 0.50 |
| Hydrogenated Castor Oil | 4.0 | 0.00 |

-continued

| Ingredients | Example I (% w/w) | Comparative Example A (% w/w) |
|---|---|---|
| Stearyl alcohol | 20.0 | 24.0 |
| Glyceryl stearate and PEG 100 Stearate | 00.0 | 1.0 |
| TOTAL | 100.0% | 100.0% |

Example I and Comparative Example A were treated in a consumer study in which approximately 118 respondents used the products at home for a one week period. It was a monadic study and all respondents were antiperspirant stick users. At the end of the one week period, subjects completed a questionnaire which evaluated product application aesthetics. An analysis of variance was performed on the data; significance was set at 90 percent. Questions 1–5 were asked and the answers were given by assigning a rating of 1–7 where 1 is "not at all" and 7 is "very". The results are given in the following Table II.

TABLE II

| CATEGORY | Example I | Comparative Example A | p-value |
|---|---|---|---|
| 1) glides on smoothly | 4.8 | 4.5 | 0.0006 |
| 2) sticky upon application | 2.2 | 2.5 | 0.0013 |
| 3) leaves a white film or residue on skin | 2.1 | 3.2 | 0.0001 |
| 4) effective in reducing perspiration | 5.3 | 4.9 | 0.0572 |
| 5) messy to use | 1.7 | 2.4 | 0.0001 |

Comparisons of Example I and Comparative Example A were done on the basis of five points using a scale of 1–5 where 1=strongly disagree and 5=strongly agree. The categories were:

1. Does not leave a white residue on skin that you can see.
2. Does not leave a residue on skin that you can feel.
3. Does not cake or build up on underarms.
4. Is a high quality product.
5. Does not leave the skin oily/greasy.

The results are shown in Table III. The p-value means the probability of observing a test statistic value which can be considered as extreme as, or more extreme than, the observed value The term "p-value" is recognized by those dealing with statistics. Usually p-value is interpreted as a measure (on a scale from 0–1) of how well the data support or discredit the null hypothesis; the smaller the p-value, the greater the evidence against the null-hypothesis. The p-values shown below indicate that all of the differences in products were statistically significant.

TABLE III

| Category | Ex. I Rating | Comparative Example A Rating | p-value |
|---|---|---|---|
| 1 | 3.8 | 3.2 | 0.0008 |
| 2 | 3.6 | 3.3 | 0.0339 |
| 3 | 3.8 | 3.3 | 0.0159 |
| 4 | 3.6 | 3.2 | 0.0181 |
| 5 | 3.9 | 3.6 | 0.0026 |

While the invention is described in connection with specific and preferred embodiments, it will be understood that it is not intended to limit the invention to those embodiments. To the contrary, it is intended to cover all alterations, modifications and equivalents as may be included within the spirit and scope of the invention as defined by the appended claims.

Throughout the present disclosure, where compositions are described as including or comprising specific components, or where processes are described as including or comprising specific processing steps, it is contemplated that compositions of the present invention also consist essentially of, or consist of, the recited components, and that the processes of the present invention also consist essentially of, or consist of, the recited processing steps.

While we have shown and described several embodiments in accordance with the present invention, it is understood that the same is not limited thereto, but is susceptible to numerous changes and modifications as known to one having ordinary skill in the art, and we therefore do not wish to be limited to the details shown and described herein, but intend to cover all such modifications as are encompassed by the scope of the appended claims.

What is claimed is:

1. A cosmetic stick composition exhibiting substantially less visible residue after application to human skin, comprising:
   (1) a gelling agent, in an amount so as to form a stick product wherein the gelling agent is selected from the group consisting of high melting point waxes having a melting point in the range of 65–101 degrees C.; and low melting point waxes having a melting point in the range of 37–65 degrees wherein said low melting point waxes can be selected from silicone waxes;
   (2) a solvent for the gelling agent, in a type and amount such that the gelling agent can dissolve therein and can gel therefrom wherein the solvent is selected from the group consisting of volatile cyclic silicones and aliphatic hydrocarbons;
   (3) a non-volatile emollient that is not a silicone and which has a refractive index of at least 1.4460, and which has adsorption and desorption properties relative to a selected active material wherein the non-volatile emollient:
      (i) is present in an amount so as to reduce any whitening effect of an active material on the skin; and
      (ii) is selected from the group consisting of
         (a) esters which are not otherwise classified as alkoxylated carboxylic acids, glyceryl esters, isethionates, lanolin derivatives, phosphorous compounds, sulfosuccinates or sulfuric acid esters;
         (b) alkoxylated alcohols wherein the alcohol portion has from 2–18 carbons and the alkylene oxide is selected from the group consisting of ethylene oxide; polyoxyethylene; and polyoxypropylene having a number of alkyleneoxide units from 2–53;
   (4) an effective amount of a cosmetically active material selected from the group consisting of deodorants and antiperspirants; and
   (5) a surfactant selected from the group consisting of ethoxylated fatty acids having 2–20 ethoxylate groups and made from fatty acids having 12–18 carbons.

2. A composition according to claim 1 which is a solid stick.

3. A composition according to claim 1 wherein the amounts of materials combined are as follows: 17–40% gelling agent; 30–50% solvent; 10–30% antiperspirant active; 10–27% nonvolatile emollient; and 1–15% surfactant, using weight percents.

4. A composition according to claim 1 wherein the gelling agent includes both high and low melting point waxes, the low melting point wax is included in the composition in an amount of 10–25 percent by weight, and the high melting point wax is included in the composition in an amount of 2–17 percent by weight of the total weight of the composition.

5. A composition according to claim 1 wherein the solvent is selected from the group consisting of volatile cyclic polydimethylsiloxanes; and aliphatic hydrocarbons having 10–32 carbons.

6. A composition according to claim 1 wherein the cosmetically active material is an antiperspirant active metal salt.

7. A composition according to claim 6 wherein the antiperspirant active ingredient is an antiperspirant metal salt, in particulate form.

8. A composition according to claim 1, wherein the composition also includes an additional whitening powder ingredient, the emollient material being included in an amount sufficient to mask a whitening effect of the additional whitening powder ingredient and of the antiperspirant active ingredient on the skin.

9. A composition according to claim 1, wherein the esters for the non-volatile emollient material are selected from the group consisting of esters derived from carboxylic acids selected from the group consisting of benzoic, lactic, palmitic, lauric and stearic acid; and alcohols selected from the group consisting of benzyl alcohol and alcohols having 12–18 carbons.

10. A composition according to claim 1, wherein the alkoxylated alcohols for the nonvolatile emollient are selected to have the alcohol portion with 2–10 carbons and the number of alkylene oxide units in the range of 4–30.

11. A composition according to claim 1, wherein the at least one non-volatile emollient material is selected from the group consisting of
   a) C12–C15 Alkyl benzoate
   b) Octyldodecyl benzoate
   c) Isostearyl benzoate
   d) Isostearyl lactate
   e) Isostearyl palmitate
   f) Isostearyl isostearate
   g) Benzyl laurate
   h) Glycereth 7 benzoate
   i) Laureth 4
   j) Laureth 7
   k) Oleth-2
   l) PEG 4
   m) PEG 12
   n) PPG 2 ceteareth 9
   o) PPG 2 isodeceth 12
   p) PPG 5 buteth 7
   q) PPG 14 butyl ether
   r) PPG 15 butyl ether
   s) PPG 53 butyl ether.

12. A composition according to claim 11 wherein the emollient is selected from the group consisting of isostearyl isostearate, isostearyl palmitate, benzyl laurate, PEG 12, and alkyl benzoates.

13. A composition according to claim 12 wherein the emollient is C12–C15 alkyl benzoate.

14. A composition according to claim 10 wherein for the alkoxylated alcohols the alcohol portion is selected from aliphatic alcohols having 2–6 carbons and the alkylene oxide portion is selected from the group consisting of ethylene oxide, polyoxyethylene, and polyoxypropylene having a number of alkylene units from 12–15.

15. A composition according to claim 4 wherein the high melting point wax is hydrogenated castor oil and the low melting point wax is stearyl alcohol.

16. A composition according to claim 1, wherein the vehicle for the gelling agent includes cyclomethicone.

17. A composition according to claim 1, wherein the composition includes, in percent by weight of the total weight of the composition, 30%–50% of the vehicle, 2%–17% high melting point wax, 10%–25% low melting point wax, 10%–30% antiperspirant metal salt, and 10%–27% non-volatile emollient material.

18. A composition according to claim 1, wherein the composition includes, in percent by weight of the total weight of the composition, 10%–27% emollient material.

19. A method for controlling perspiration wetness, comprising applying the antiperspirant stick composition of claim 1 to axillary regions of a human.

20. A method for controlling perspiration wetness, comprising applying the antiperspirant stick composition of claim 2 to axillary regions of a human.

21. A method for controlling perspiration wetness, comprising applying the antiperspirant stick composition of claim 9 to axillary regions of a human.

22. A method for controlling perspiration wetness, comprising applying the antiperspirant stick composition of claim 11 to axillary regions of a human.

23. An antiperspirant stick composition which is made by combining:
   (1) a gelling agent, in an amount so as to form a stick product wherein the gelling agent is selected from the group consisting of high melting point waxes having a melting point in the range of 65–101 degrees C.; and low melting point waxes having a melting point in the range of 37–65 degrees wherein said low melting point waxes can be selected from silicone waxes;
   (2) a solvent for the gelling agent, in a type and amount such that the gelling agent can dissolve therein and can gel therefrom wherein the solvent is selected from the group consisting of volatile cyclic silicones; and aliphatic hydrocarbons;
   (3) a non-volatile emollient that is not a silicone and which has a refractive index of at least 1.4460, and which has adsorption and desorption properties relative to a selected antiperspirant active wherein the non-volatile emollient:
      (i) is present in an amount so as to reduce any whitening effect of the antiperspirant active on the skin; and
      (ii) is selected from the group consisting of
         (a) esters which are not otherwise classified as alkoxylated carboxylic acids, glyceryl esters, isethionates, lanolin derivatives, phosphorous compounds, sulfosuccinates or sulfuric acid esters;
         (b) alkoxylated alcohols wherein the alcohol portion has from 0–18 carbons and the alkylene oxide is selected from the group consisting of ethylene oxide; polyoxyethylene; and polyoxypropylene; and
   (4) an effective amount of a cosmetically active material selected from the group consisting of deodorants and antiperspirants; and (5) a surfactant selected from the group consisting of ethoxylated fatty acids having 2–20 ethoxylate groups and made from fatty acids having 12–18 carbons.

24. The antiperspirant stick composition according to claim 1 further comprising a bacteriostat.

25. The antiperspirant stick composition according to claim 24 wherein the bacteriostat is added in an amount of 0.05–1.0% by weight of the total weight of the composition.

26. The antiperspirant stick composition according to claim 24 wherein the bacteriostat is selected from the group consisting of quaternary ammonium compounds and zinc salts.

27. The antiperspirant stick composition according to claim 26 wherein the bacteriostat is a quaternary ammonium compound selected from the group consisting of 2-amino-2-methyl-1-propanol; cetyl-trimethylammonium bromide; cetyl pyridinium chloride; 2,4,4N-trichloro-2N-hydroxydiphenylether; and N-(-4-chlorophenyl)-N'-(3,4-dichlorophenyl)urea.

28. The antiperspirant stick composition according to claim 1 further comprising a fragrance.

29. The antiperspirant stick composition according to claim 28 wherein the fragrance is added in an amount of 0.5–3.0% by weight of the total weight of the composition.

30. The antiperspirant stick composition according to claim 1 further comprising an inert filler.

31. The antiperspirant stick composition according to claim 29 wherein the inert filler is selected from the group consisting of corn starch, talc, fumed silica, inorganic clays, polyethylene and mixtures of the foregoing.

32. The antiperspirant stick composition according to claim 30 comprising cyclomethicone, C12–C15 alkyl benzoate; aluminum zirconium tetrachlorohydrex glycine complex; PEG-8 distearate; fragrance; starch; hydrogenated castor oil; stearyl alcohol; and isostearyl benzoate.

33. The antiperspirant stick composition according to claim 2 wherein the at least one non-volatile emollient material is $C_{12}$–$C_5$ alkyl benzoate.

34. The antiperspirant stick composition according to claim 3 wherein the at least one non-volatile emollient material is $C_{12}$–$C_{15}$ alkyl benzoate.

35. The antiperspirant stick composition according to claim 34 further comprising a bacteriostat.

* * * * *